US009265530B2

(12) United States Patent
Llas Vargas et al.

(10) Patent No.: US 9,265,530 B2
(45) Date of Patent: Feb. 23, 2016

(54) APPARATUS AND METHODS FOR FIXATING A CRANIAL BONE FLAP WITH A CRANIAL BONE MASS

(71) Applicant: Neos Surgery S.L., Cerdanyola del Vallès (Barcelona) (ES)

(72) Inventors: Salvador Llas Vargas, Lleida (ES); Pau Garcia Roig, Girona (ES); Lluis Chico Roca, Badalona (ES)

(73) Assignee: NEOS SURGERY S.L., Barcelona (ES)

( * ) Notice: Subject to any disclaimer, the term of this patent is extended or adjusted under 35 U.S.C. 154(b) by 588 days.

(21) Appl. No.: 13/719,005

(22) Filed: Dec. 18, 2012

(65) Prior Publication Data
US 2014/0171944 A1 Jun. 19, 2014

(51) Int. Cl.
*A61B 17/80* (2006.01)
*A61B 17/68* (2006.01)
*A61B 17/88* (2006.01)

(52) U.S. Cl.
CPC ............... *A61B 17/688* (2013.01); *A61B 17/68* (2013.01); *A61B 17/80* (2013.01); *A61B 17/8061* (2013.01); *A61B 17/8872* (2013.01)

(58) Field of Classification Search
CPC ...... A61B 17/68; A61B 17/688; A61B 17/80; A61B 17/8061; A61B 17/8872
See application file for complete search history.

(56) References Cited

U.S. PATENT DOCUMENTS 3,926,193 A 12/1975 Hasson
4,119,091 A 10/1978 Partridge
4,456,006 A 6/1984 Wevers et al.
5,449,359 A 9/1995 Groiso
5,743,913 A 4/1998 Wellisz
5,788,698 A 8/1998 Savornin
5,810,854 A 9/1998 Beach
6,022,351 A 2/2000 Bremer et al.
(Continued)

FOREIGN PATENT DOCUMENTS

DE 20315612 U1 12/2003
DE 10347173 * 6/2005 ............. A61B 17/68
(Continued)

OTHER PUBLICATIONS

Spanish Search Report for ES2336059, dated Mar. 22, 2010, 2 pages, issued by The Spanish Office of Patent and Trademarks, Madrid, Spain (Partial Translation).
(Continued)

*Primary Examiner* — Larry E Waggle, Jr.
(74) *Attorney, Agent, or Firm* — Edell, Shapiro & Finnan, LLC

(57) ABSTRACT

A fixation device for use in securing a cranial bone flap with a cranial bone mass at the location of a burr hole. In one implementation the fixation device includes a closure plate having a substrate with an outer surface and an inner surface and with at least a portion of the inner surface adapted to be applied against the outer face of the outer edges of the cranial bone mass and the cranial bone flap at the location of the burr hole. The closure plate is also adapted with a burr hole fitting coupled to and spaced a distance below the inner surface of the substrate and adapted for being inserted entirely into the burr hole. The fitting may include one or more peripheral portions adapted for being pressed against the inner wall of the burr hole when the fitting is inserted therein. The peripheral portions are endowed with a freedom of movement that enables the fitting to be inserted into the burr hole.

37 Claims, 22 Drawing Sheets

(56) References Cited

U.S. PATENT DOCUMENTS

| | | | |
|---|---|---|---|
| 6,050,998 | A | 4/2000 | Fletcher |
| 6,126,663 | A * | 10/2000 | Hair .............................. 606/324 |
| 6,589,246 | B1 | 7/2003 | Hack et al. |
| 6,921,401 | B2 | 7/2005 | Lerch et al. |
| 6,969,391 | B1 | 11/2005 | Gazzani |
| 7,238,188 | B2 | 7/2007 | Nesper et al. |
| 7,833,253 | B2 * | 11/2010 | Ralph et al. ................... 606/283 |
| 8,403,930 | B2 | 3/2013 | Chico Roca |
| 2004/0034375 | A1 * | 2/2004 | Ruiz et al. ...................... 606/151 |
| 2004/0102779 | A1 | 5/2004 | Nesper et al. |
| 2004/0116961 | A1 | 6/2004 | Nesper et al. |
| 2005/0240189 | A1 | 10/2005 | Rousseau et al. |
| 2006/0015106 | A1 | 1/2006 | Lerch et al. |
| 2006/0259040 | A1 | 11/2006 | Wellisz et al. |
| 2007/0270856 | A1 | 11/2007 | Morales et al. |
| 2008/0039837 | A1 * | 2/2008 | Gambale ......................... 606/60 |
| 2008/0172097 | A1 | 7/2008 | Lerch et al. |
| 2008/0281339 | A1 * | 11/2008 | Kirschman ................... 606/151 |
| 2012/0136397 | A1 | 5/2012 | Ralph et al. |

FOREIGN PATENT DOCUMENTS

| | | | | |
|---|---|---|---|---|
| DE | 10347173 | B3 | 6/2005 | |
| DE | 10360852 | * | 7/2005 | ............ A61B 17/58 |
| EP | 0201905 | A2 | 11/1986 | |
| EP | 1171050 | B1 | 10/2004 | |
| EP | 1477122 | A2 | 11/2004 | |
| FR | 2357229 | A1 | 2/1978 | |
| JP | 2001-25141 | A | 1/2001 | |
| JP | 2003-512885 | A | 4/2003 | |
| WO | WO0049949 | A1 | 8/2000 | |

OTHER PUBLICATIONS

International Search Report and Written Opinion of the International Searching Authority (Corrected Version), International Application No. PCT/EP2008/060279, Date of mailing Apr. 29, 2009, 16 pages, issued by the European Patent Office, Rijswijk Netherlands.

English Translation of the "Notice of Grounds for Rejection" issued by the Japanese Patent Office on JP Patent Application No. 2010-519454, Feb. 5, 2013, 2 pages, Tokyo Japan.

International Search Report and Written Opinion of the International Searching Authority, International Application No. PCT/EP2013/077100, Date of mailing Feb. 21, 2014, 13 pages, issued by the European Patent Office, Rijswijk Netherlands.

* cited by examiner

APPARATUS AND METHODS FOR FIXATING A CRANIAL BONE FLAP WITH A CRANIAL BONE MASS

TECHNICAL FIELD

The invention relates to apparatus and methods for fixating a cranial bone flap with a cranial bone mass.

BACKGROUND

A craniotomy is a surgical procedure that involves a cut that opens the cranium. During this type of surgical procedure, a section of the skull, called a bone flap, is removed to access that portion of the brain underneath. A craniotomy is performed by lifting and folding back the skin and muscle from the bone. Next, one or more small burr holes are made in the skull with a drill. The surgeon then inserts a special saw through the burr holes to cut the outline of the bone flap. The cut bone flap is lifted and removed to expose the protective covering of the brain called dura. The bone flap is safely stored until it is replaced at the end of the procedure.

The replacement of the bone flap is generally achieved by the use of plates and screws or the use of cranial flap clamps. The use of cranial flap clamps typically involves the use of inner and outer plates that are interconnected and placed on respective opposite sides of the bone flap and cranial bone mass where they are pressed against the inner and outer surfaces of the bone flap and cranial bone mass to effectuate the fixation of the bone flap. U.S. Publication No. 2010/0298828 A1 discloses apparatus and methods involving the use of cranial flap clamps. FIG. 1, illustrates a prior art bone flap fixation device that is disclosed and described in U.S. Publication No. 2010/0298828 A1. The fixation device 1 includes a support plate 2 with an inner surface 3 that is adapted to be applied against the inner face of the outer edges of the cranial bone mass and the bone flap. A first flexible strip segment 4a extends from a first peripheral edge of the support plate and a second flexible strip segment 4b extends from a second peripheral edge of the support plate. The fixation device 1 also includes a closure plate 5 with an outer surface 6 and an inner surface 7 with the inner surface adapted to be applied against the outer face of the outer edges of the cranial bone mass and the bone flap. The closure plate has first and second openings 9a, 9b extending there through that are each adapted to respectively receive the first and second flexible strip segments 4a, 4b. Each of the first and second openings 9a, 9b include an interlocking feature that permits the closure plate 5 to be moved along strips 4a, 4b only in a direction towards the support plate 2. The ends of strips 4a, 4b are attached to respective ends of a handle 10. In use, when the support plate 2 has been properly positioned to overlap and rest against the inner surfaces of the bone flap and cranial bone mass, the closure plate 5 is advanced towards the support plate 2 until the inner surface 7 of the closure plate overlaps and rests against the outer surfaces of the bone flap and cranial bone mass.

SUMMARY OF THE DISCLOSURE

According to some implementations a closure plate is provided for use in fixating a cranial bone flap with a cranial bone mass at the location of a burr hole having an inner wall, the closure plate comprising: a substrate having an outer surface and an inner surface, at least a portion of the inner surface adapted to be applied against the outer face of the outer edges of the cranial bone mass and the cranial bone flap at the location of the burr hole; the closure plate further comprising a burr hole fitting coupled to and spaced a distance below the inner surface of the substrate and adapted for being inserted entirely into the burr hole, the fitting comprising one or more peripheral portions adapted for being pressed against or resting on the inner wall of the burr hole when the fitting is inserted therein, the one or more peripheral portions endowed with a freedom of movement, the freedom of movement of the one or more peripheral portions enabling the fitting to be inserted into the burr hole.

According to some implementations a support plate is provide for use in fixating a cranial bone flap with a cranial bone mass at the location of a burr hole having an inner wall, the support plate comprising: a substrate having an outer surface and an inner surface, at least a portion of the inner surface adapted to be applied against the inner face of the outer edges of the cranial bone mass and the cranial bone flap at the location of the burr hole; and a burr hole fitting coupled to and spaced a distance above the inner surface of the substrate and adapted for residing entirely into the burr hole, the fitting comprising one or more peripheral portions adapted for being pressed or rested against the inner wall of the burr hole when the fitting resides therein, the one or more peripheral portions endowed with a freedom of movement, the freedom of movement of the one or more peripheral portions enabling the fitting to reside within the burr hole.

According to other implementations a fixation device for fixating a cranial bone flap with a cranial bone mass at the location of a burr hole having an inner wall, the fixation device comprising: a support plate having an inner surface that is adapted to be applied against the inner face of the outer edges of the cranial bone mass and the cranial bone flap at the location of the burr hole, the inner surface having a peripheral profile comprising first and second peripheral edges, the peripheral profile being of a size sufficient for at least portions of the inner surface to extend across the outer edges of the cranial bone mass and the cranial bone flap at the location of the burr hole; a first flexible strip segment extending from the first peripheral edge of the support plate and a second flexible strip segment extending from the second peripheral edge of the support plate; and a closure plate having an outer surface and an inner surface, the inner surface adapted to be applied against the outer face of the outer edges of the cranial bone mass and the cranial bone flap at the location of the burr hole, the closure plate having first and second openings extending there through, each of the first and second openings respectively receiving the first and second flexible strip segments, each of the first and second openings having associated therewith an interlocking feature that permits the passage and movement of the first and second flexible strip segments in a first direction through the respective first and second openings while preventing movement of the first and second flexible strip segments in a second direction opposite the first direction, the closure plate being moveable along the first and second flexible strips in a direction toward the support plate, the closure plate further comprising a burr hole fitting coupled to and spaced a distance below the inner surface of the substrate and adapted for being inserted entirely into the burr hole, the fitting comprising one or more peripheral portions adapted for being pressed against or rest on the inner surface of the burr hole when the fitting is inserted therein, the one or more peripheral portions endowed with a freedom of movement, the freedom of movement of the one or more peripheral portions enabling the fitting to be inserted into the burr hole.

DETAILED DESCRIPTION

As discussed above, craniotomies that involve the removal of a bone flap generally require the formation of one or more burr holes. The burr holes are formed by the use of drills that today typically come in two sizes, 11 millimeter and 14 millimeter. When, for example, a 14 millimeter drill size is used, a burr hole having a diameter of between 14.0 and 14.3 millimeters is generally produced. In accordance with the apparatus and methods disclosed herein, the fixation of a cranial bone flap with a cranial bone mass at the location of the burr hole(s) is made possible regardless of the size of the burr hole. However, for purposes of discussion, the dimensional characteristics provided herein are predominately directed to fixation devices intended for use with burr holes produced by a 14 millimeter drill size.

Figure 1:
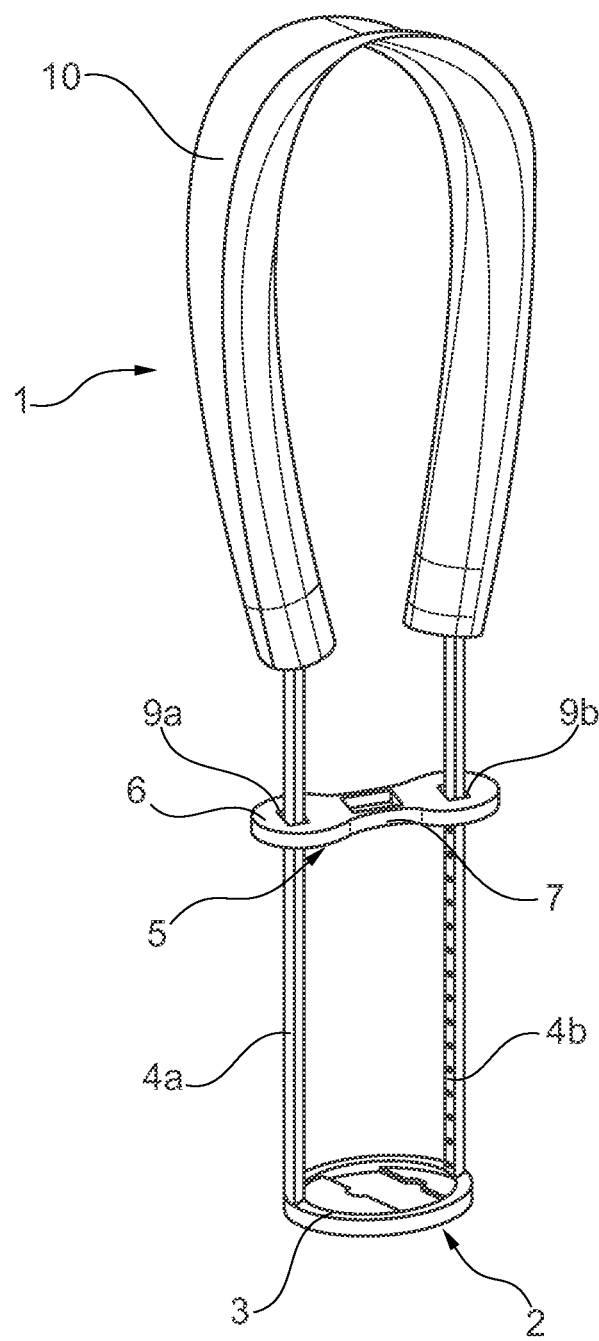
FIG. 1 illustrates a prior art bone flap fixation device.
Figure 10:
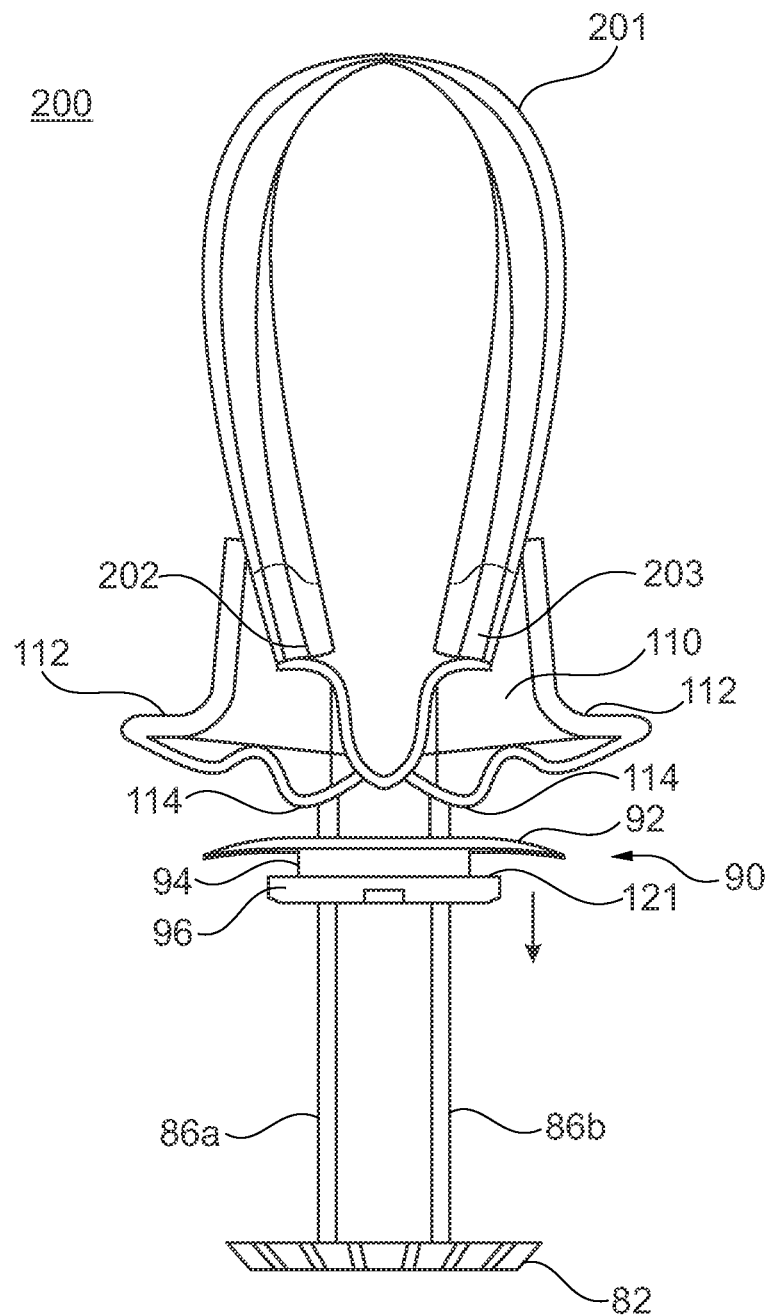
FIG. 10 illustrates a bone flap fixation device according to an implementation.

As discussed above, the manner in which clamps are used to fixate a bone flap to the cranial bone mass of a patient typically involves the placement of plates on opposite inner and outer surfaces of the bone flap and cranial bone mass. These plates are referred to herein as closure and support plates with the support plate adapted to be applied against the inner surface and the closure plate adapted to be applied against the outer surface. As with the fixation device illustrated in FIG. 1, bone flap fixation is generally achieved by first situating the support plate against the inner surface of the cranial bone mass, replacing the bone flap, and then advancing the closure plate over a guide that connects the two plates until the closure plate rests against the outer surfaces of the bone flap and cranial bone mass. In the fixation device of FIG. 1, the guide is provided in the form of first and second flexible strips 4a and 4b. With respect to the bone flap fixation devices disclosed and contemplated herein, the support and closure plates may also be connected by first and second flexible strip segments. FIG. 10 depicts such an implementation. It is to be appreciated however, that the implementations disclosed and contemplated herein are not limited to such a configuration and that any of a variety of singular or multiple guides, whether flexible or inflexible, may be used without deviating from the spirit and scope of the invention.

Figure 2A:
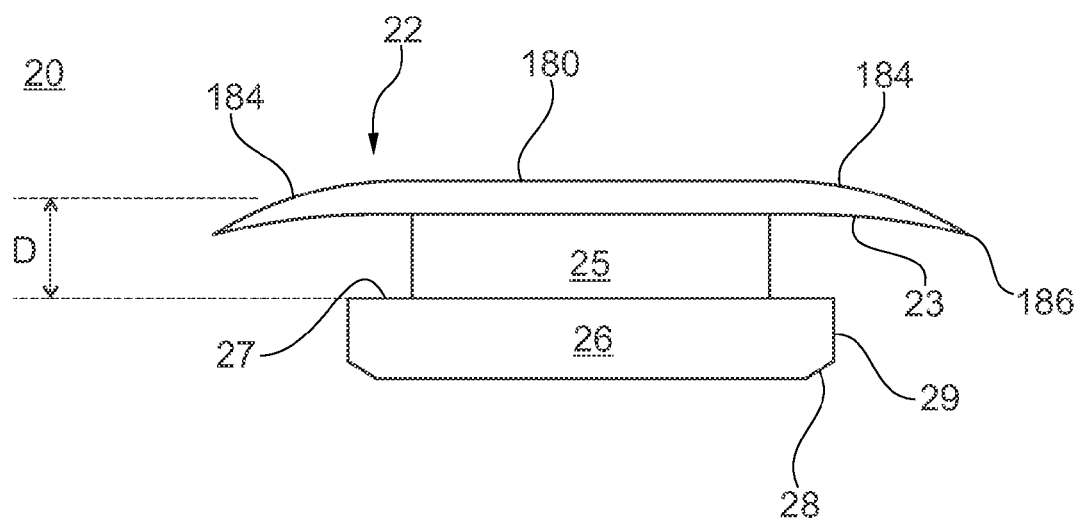
FIG. 2A illustrates a closure plate prior to use according to an implementation.
Figure 6:
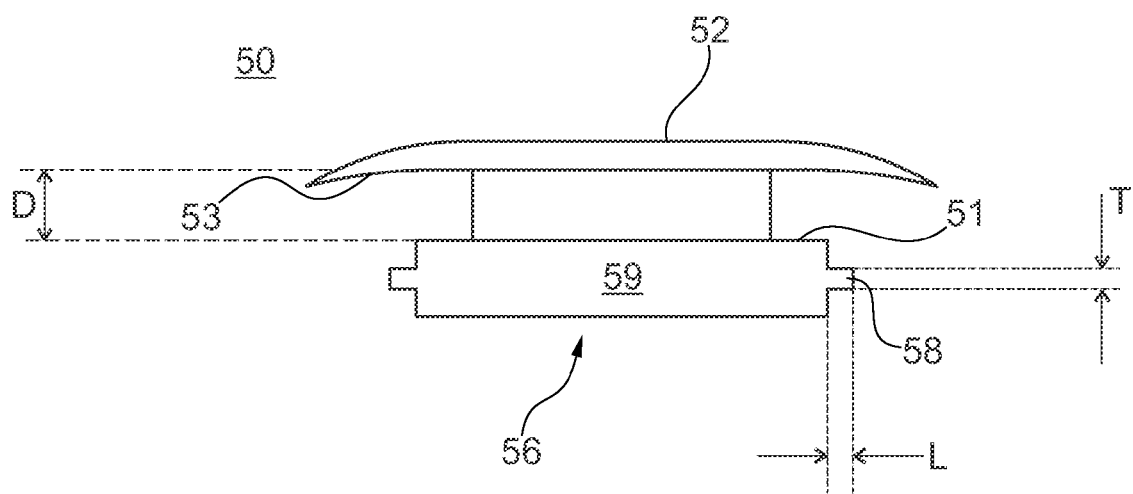
FIG. 6 illustrates a closure plate according to an implementation.

FIG. 2A illustrates a closure plate 20 according to an implementation that comprises a substrate 22 with an inner surface 23 adapted to be applied against the outer face of the outer edges of the bone flap and cranial bone mass. The closure plate 20 further includes a burr hole fitting 26 that resides below the inner surface 23 of the substrate 22. The fitting 26 is attached to a spacer 25 that extends downward from the substrate 22. In some implementations the spacer 25 is formed integrally and as a single piece with the substrate 22. That is, the substrate 22 and spacer 25 comprise a monolithic structure. In other implementations the spacer 25 is produced as a separate part and later attached or otherwise coupled with the substrate 22. The attachment or coupling may comprise many forms including mere contact. In other implementations, the spacer 25 and fitting 26 comprise a monolithic structure with the spacer 25 being attached to or otherwise coupled with the substrate 22. In yet other implementations the substrate 22, spacer 25 and fitting 26 comprise a monolithic structure. It is important to note as well that the spacer 25 may also take many forms. In FIGS. 2A and 6 the spacer is generally shown as a single column-like structure that extends downward from the inner surface of the substrate. In such implementations the column-like structure may comprise a hollow interior for housing at least a part of the spacer. In other implementations the spacer is simply attached to a bottom surface or bottom portion of the spacer. In yet other implementations the spacer comprises features such as, for example grooves, receptacles or the like for receiving cooperating features of the fitting for the purpose of coupling the fitting to the spacer. Features may also be provided in the spacer for cooperating with features of the fitting for the purpose of properly positioning the fitting a spaced-apart distance from the substrate. The implementations of FIGS. 10-13 (see below) provide examples of such features. Other spacer configurations comprising non-column-like structures are also contemplated.

Figure 2B:
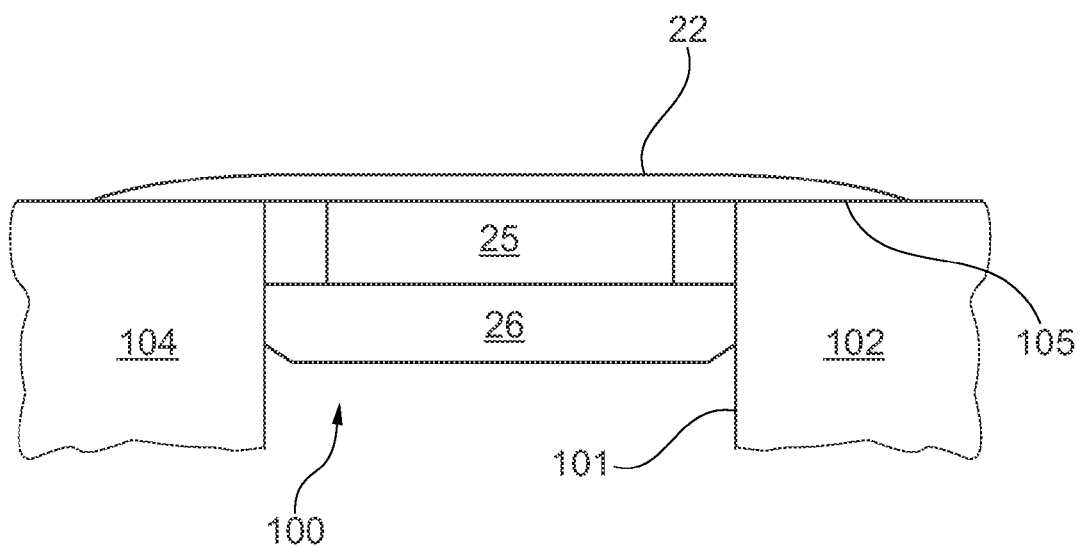
FIG. 2B illustrates the closure plate of FIG. 2A after the closure plate has been applied firmly against the outer face of the outer edges of the bone flap and cranial bone mass.
Figure 2C:
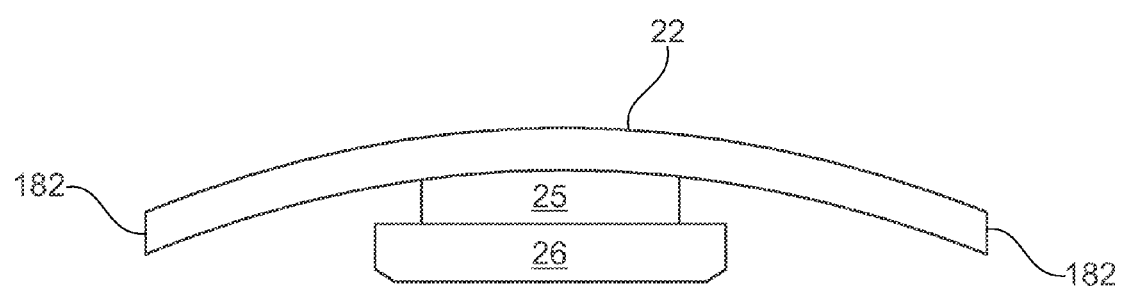
FIG. 2C illustrated a closure plate according to other implementations.

With continued reference to FIG. 2A, the purpose of the spacer 25, regardless of its structure, is to maintain a spaced-apart relationship between the upper part 27 of the fitting 26 and the inner surface 23 of the substrate 22 when the closure plate 20 is applied firmly against the outer face 105 of the outer edges of the bone flap 102 and cranial bone mass 104 at the location of the burr hole 100 as shown in FIG. 2B. In some implementations, the substrate 22, spacer 25 and fitting 26 are structured and interconnected in a manner that results in all portions of the substrate 22 to be always spaced a distance apart from the fitting 26, as shown in FIG. 2A. That is, both before and after being firmly applied against the outer face 105 of the outer edges of the bone flap 102 and cranial bone mass 104, all portions of the substrate maintain a spaced-apart relationship with all, or essentially all, of the fitting 26. In other implementations, as shown in FIG. 2C, when the fixation device is in an assembled and ready to use position (like the position shown in FIG. 10), one or more outer radial portions 182 of the substrate 22 are not spaced-apart from the fitting 26. For example, in some implementations the bottom-most portion of the substrate 22 and the top-most portion of the fitting 26 lie in the same or substantially same plane. In other implementations the bottom-most portion of the substrate 22 lies below the top-most portion of the fitting 26.

According to one implementation the burr hole fitting 26 is made of a resilient material and is configured and sized to be inserted into the burr hole 100 to a prescribed depth below the outer face 105. The configuration and size of the fitting 26 also results in at least a peripheral portion 29 of the fitting being rested or pressed against an inner wall 101 of the burr hole 100 when the closure plate 20 is applied against the outer surface 105 as shown in FIG. 2B. The lower edge 28 of the fitting 26 may be chamfered as shown in FIG. 2A to facilitate the introduction of the fitting 26 into the burr hole 100. Absent the resilient nature of the material in which the fitting 26 is made, in some implementations the fitting 26 would be prohibited from being inserted into the burr hole 100. In some implementations, the entirety of the fitting 26 is made of a resilient material, such a plastic or rubber material. In other implementations only portions of the fitting 26 are endowed with resiliency, the resilient portions enabling the peripheral portions 29 to move radially inward and/or fold/bend upward as the fitting is pressed into the burr hole 100.

The burr hole fitting 26 and the manner in which it is incorporated into the closure plate 20 may take many forms. What is important is that, regardless of the closure plate structure, there exist a spaced-apart relationship between the upper part 27 of the fitting 26 and the inner surface 23 of the substrate 22 when the closure plate 20 is applied firmly against the outer face 105 of the outer edges of the bone flap 102 and cranial bone mass 104. This feature facilitates a proper and complete placement of the burr hole fitting 26 into the burr hole and ensures that no portion of the fitting 26 interferes with the substrate's 22 ability to conform with the outer surface of the patient's scalp when the closure plate 20 is applied thereto. It is also desirable that at least a peripheral portion of the fitting 26 rests against or is urged against an inner wall 101 of the burr hole 100. In the case where the peripheral portion of the fitting is to be urged or otherwise pressed against the inner wall 101 of the burr hole 100, the resiliency is manifested by one or more portions of the fitting undergoing a compression, flexion, or the like. An advantage of the burr hole fitting 26 is that it provides the fixation device with an ability to self-center and/or be stabilized within the burr hole 100 during use.

Figure 5:
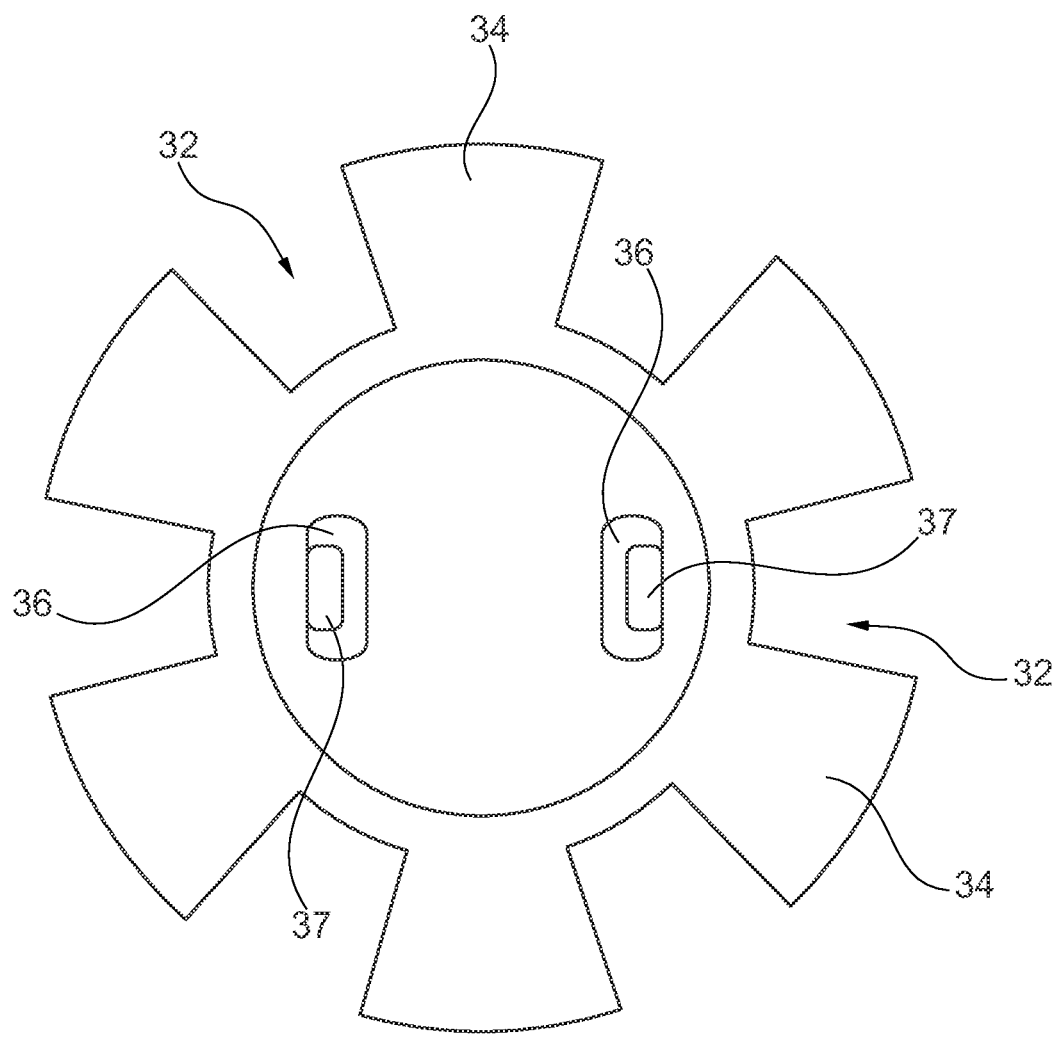
FIG. 5 illustrates a bottom view of the closure plate substrate of FIG. 2 according to one implementation.

In the implementations of FIG. 2 the substrate 22 comprises a substantially flat central portion 180 one or more radial outer portions 184 defined by areas of curvature and/or areas of inclination as shown in FIG. 2A. The substrate 22 is also provided with a sufficient degree of flexibility that permits the substrate 22 to conform with the patient's scalp when it is applied to an outer surface 105 of the scalp as shown in FIG. 2B. Flexibility may be achieved by providing free areas 32 in the substrate 22 to produce flanges 34 as shown in FIG. 5. In some implementations the substrate 22 is endowed with at least some resiliency so that the curved and/or inclined areas provide a type of spring action that acts against the force applied between the closure plate and support plate when the bone flap has been secured to the cranial bone mass between the support plate and the closure plate.

As shown in FIG. 2A, in some implementations the thickness profile of the substrate 22 may vary along its radius. In the implementations of FIG. 2A, the thickness of the substrate is greatest at or near the center portion 180 with the thickness diminishing to a minimum thickness at the peripheral edge 186 of the radial outer portions 184. Such a construction results in a substrate having a strong central core and an outer radially extending section that has an ability to flex or bend. Providing a minimum thickness at the peripheral edge 186 that results in a pointed or nearly pointed configuration, as shown in FIG. 2A, enhances the substrate's ability to partially penetrate into the upper surface 105 of the bone flap 102 and cranial bone mass 104 when the inner surface 23 of the substrate 22 is firmly applied against the outer surface 105. Integration of at least a portion of the substrate 22 into the outer surface 105 reduces the likelihood of having the substrate 22 slip along the surface 105 once the substrate has been applied thereto.

In some implementations the entirety of the components that form the closure plate 20 are made of a polymeric material, such as polyetheretherketone (PEEK). The use of PEEK and like materials advantageously provides the closure plate with a significant degree of radiotransparency. In other implementations the components that form the closure plate 20 are made of a combination of materials that may include plastics, metals, composites, etc. As an example, in the implementation of FIG. 4A the substrate 22 of the closure plate 20 is made of a polymeric material, such as PEEK, with the inner surface 23 of the substrate coated with or otherwise lined with a non-polymeric layer 24. The non-polymeric layer 24 may be provided with a hardness and a surface roughness that permits it to be at least partially embedded into the outer surface 105 of the scalp when the closure plate 20 is applied firmly against the outer face 105 of the outer edges of the bone flap 102 and cranial bone mass 104. Such a feature inhibits the closure plate 20 from slipping along the outer surface 105 after it has been affixed thereto. In some implementations the non-plastic layer 24 may comprise a metal, such as titanium. In other implementations the layer 24 may comprise a vapour deposited diamond layer. The layer may encompass the entirety of the inner surface 23 of the substrate 22 or only portions thereof. For example, in some implementations only an outer peripheral rim or region of the inner surface 23 is provided with the layer 24. According to other implementations the non-slip feature is achieved by coating or lining the inner surface 23 of the substrate 22 with a tacky or adhesive substance 30 as shown in FIG. 4B.

Figure 3A:
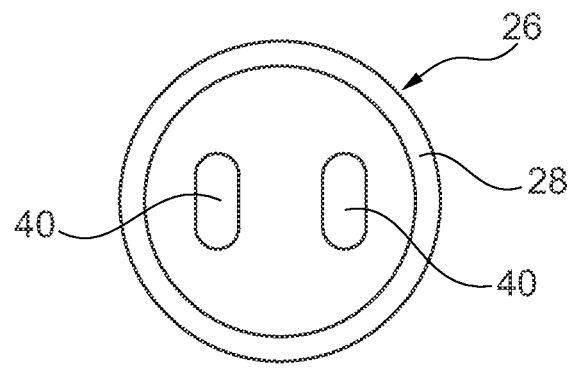
FIGS. 3A-3E illustrate bottom views of the burr hole fitting of FIG. 2 according to different implementations.
Figure 3B:
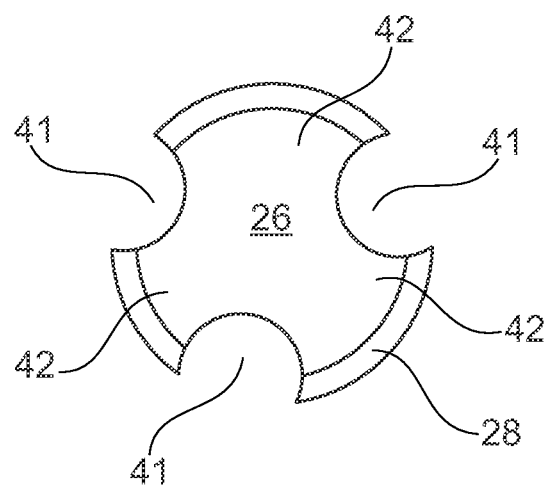
Figure 3C:
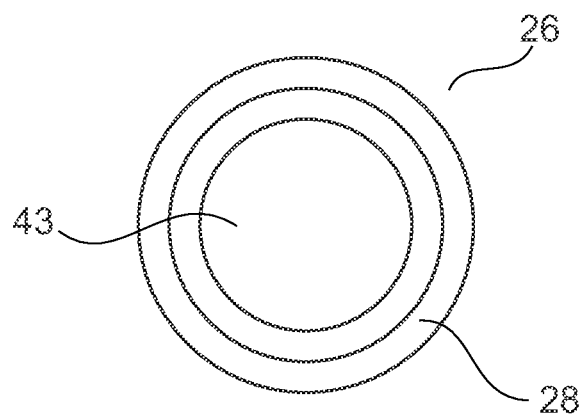
Figure 3D:
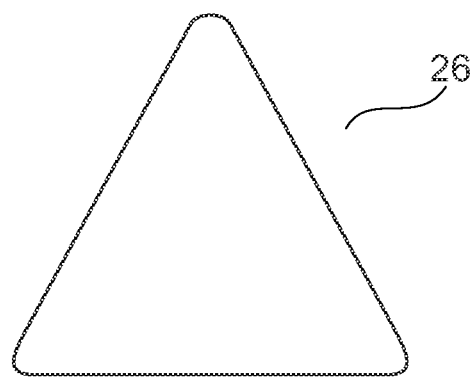
Figure 3E:
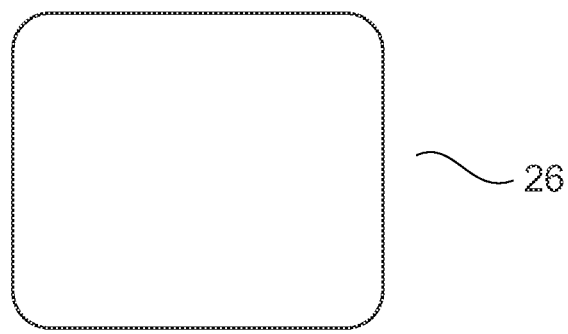

FIGS. 3A-E show bottom views of the fitting 26 according to different implementations. In some implementations the fitting 26 has a circular shape as shown in FIG. 3A. In such implementations one or more openings 40 may be provided in the fitting 26 to facilitate the passage of flexible strips or other means by which the closure plate 20 is connected with the support plate. In the implementation of FIG. 3B the fitting 26 includes open areas 41 to produce three radially extending members 42. Fewer or more than three open areas 41 may be provided to produce fewer or more radially extending members 42. The inclusion of the open areas 41 provides a number of advantages. First, it results in a reduction of the amount of material necessary to produce the fitting. Second, the open areas 41 may be used to facilitate the passage of flexible strips or other means by which the closure plate 20 is connected with the support plate. Third, the existence of multiple spaced-apart radially extending members 42 enables the areas of the fitting that contact the inner wall 101 of the burr hole 100 to more easily adapt to the inner wall profile. As shown in FIG. 3C, in other implementations a fitting 26 having a hollow interior 43 may be provided. As with the implementation of FIG. 3B, the implementation of FIG. 3C results in a reduction of the amount of material necessary to produce the fitting and provides a passage for accommodating flexible strips or other means by which the closure plate 20 is connected with the support plate. Also, by altering the size and/or shape of the hollow interior, the mechanical properties (e.g., flexibility, compressibility, etc.) of the fitting of FIG. 3C can be more readily adjusted to achieve particular design requirements.

In the implementations of FIGS. 3A-C the shape of the fitting is derivable from a circular or circular like construct. However, this is not a requirement. For example, in other implementations the burr hole fittings has shapes derivable from, triangular (see FIG. 3D), quadrilateral (see FIG. 3E) and even elliptical constructs.

In other implementations cuts, grooves, ribs, or other like features may be incorporated into the fitting 26 to achieve particular localized and/or global burr hole fitting properties.

Turning again to FIG. 5, in some implementations the closure plate 20 has one or more openings 36 extending there through that are adapted to receive one or more flexible strips or other means by which the closure plate 20 is connected with the support plate. In the closure plate of FIG. 5, first and second openings are provided for respectively receiving first and second flexible strip segments that are coupled with and extend from a support plate. The construction of the openings 36 is similar to that described above in conjunction with the prior art device depicted in FIG. 1 with each of the first and second openings 36 having associated therewith an interlocking feature 37 that permits the passage and movement of the first and second flexible strip segments in a first direction through the respective first and second openings 36 while preventing movement of the first and second flexible strip segments in a second direction opposite the first direction.

As discussed above, a common burr hole size is in the range of 14.0 to 14.3 millimeters in diameter. According to some implementations the closure plate adapted for such a burr hole size is provided with substrate diameter of between about 16 to about 23 millimeters. The dimensions of the burr hole fitting 26 in such applications may be in some implementations between about 14.35 to about 14.40 millimeters in diameter and between about 1.0 to about 5.0 millimeters in thickness, preferably between about 1.0 to about 2.0 millimeters in thickness. Further, as discussed above, it is desirable that the fitting 26 be spaced a distance D away from the inner surface 23 of the closure plate substrate 22 so that a spaced-relationship is maintained between the upper surface 27 of the fitting 26 and the inner surface 23 of the substrate 22 when the closure plate 20 has been properly secured to the outer face 105 as depicted in FIG. 2B. According to some implementations the distance D (see FIG. 2A) is between about 0.1 to about 10.0 millimeters, and preferably between about 0.2 to about 1.5 millimeters. In some implementations the closure plate substrate 22 comprises an elliptical shape having both major and minor dimensions that fall within the about 16 to about 23 millimeter range.

Figure 8:
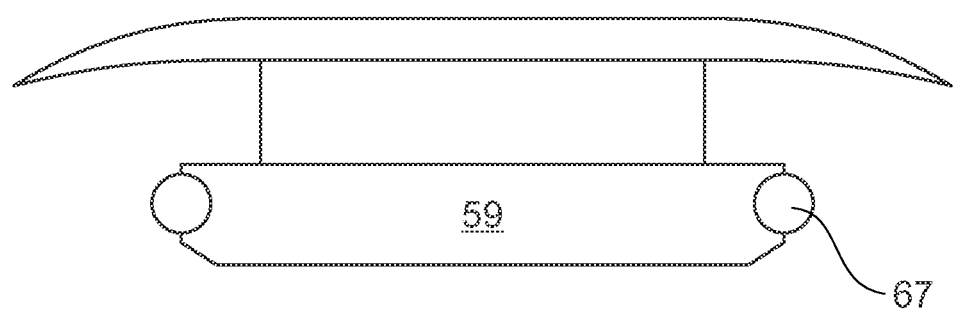
FIG. 8 illustrates a closure plate according to an implementation.

FIG. 6 depicts a closure plate 50 according to other implementations. In such implementations the fitting 56 is equipped with a peripheral lip 58 that has a diameter that is equal to and preferably greater than that of the burr hole 100. The peripheral lip 58 is adapted to flex and/or be compress in order to be pressed or to otherwise rest against the inner wall 101 of the burr hole 100 when the fitting 56 is inserted therein. In some implementations the peripheral lip 58 is integrally formed as a single piece with the structure 59 that supports it. For example, in one implementation the support structure 59 and peripheral lip 58 are injection molded as a single unit from a polymeric material, such as PEEK. In other implementations the lip 58 is formed separately from the support structure 59 and is attached or otherwise coupled thereto. For example, the lip 58 may comprise an outer circumferential surface of an elastomeric o-ring 67 that resides within a groove of the support structure 59 as shown in FIG. 8.

Figure 7A:
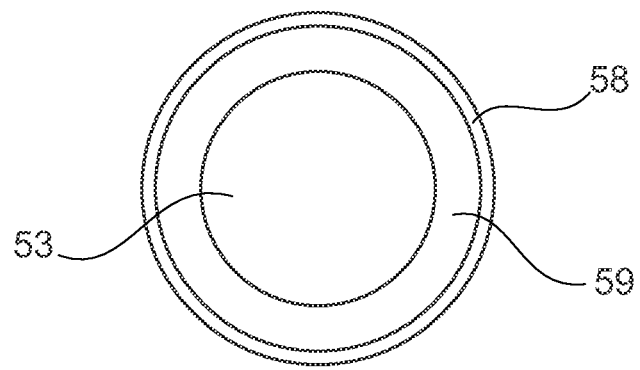
FIGS. 7A-C illustrate bottom views of the burr hole fitting of FIG. 6 according to different implementations.
Figure 7B:
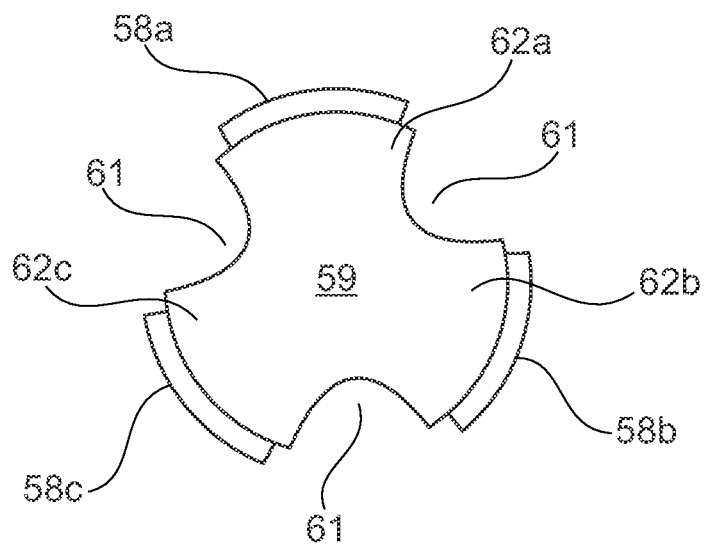
Figure 7C:
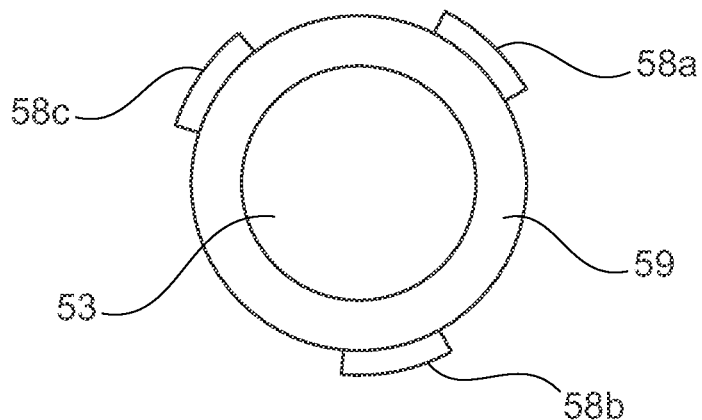

The support structure 59 may comprise a circular substrate, a circular ring as shown in FIG. 7A, or other shapes, including, but not limited to those depicted in FIGS. 7B and 7C. In the implementation of FIG. 7A the support structure 59 comprises a circular ring with the peripheral lip 58 extending around the entire circumference of the support structure 59. In the implementation of FIG. 7C, the peripheral lip 58 comprises circumferentially and equidistantly-spaced lip segments 58a, 58b and 58c. In the implementation of FIG. 7B the fitting 56 includes open areas 61 to produce three radially extending members 62a, 62b and 62c. Fewer or more than three open areas 61 may be provided to produce fewer or more radially extending members 62. In the implementation of FIG. 7B the peripheral lip 58 comprises lip segments 58a, 58b and 58c that respectively extend radially from members 62a, 62b and 62c. As discussed above in conjunction with the implementations of FIGS. 3A-C, the openings 53 and open areas 61, as the case may be, may provide a passage for accommodating the flexible strips or other means by which the closure plate 20 is connected with the support plate.

In some implementations, one or more portions of the support structure 59, or the entirety of the support structure 59, are endowed with a certain degree of compressibility and/or flexibility to provide with the peripheral lip 58 a burr hole fitting 58 compatible with being inserted and housed within the interior of the burr hole 100.

According to some implementations the closure plate substrate 52 has a diameter of between about 16 to about 23 millimeters. The diameter of the burr hole fitting 56 as measured from the outer bounds of the peripheral lip 58 in such applications may be in some implementations between about 14.35 to about 14.40 millimeters. According to some implementations the peripheral lip 58 has a thickness T of about 0.05 millimeters and a length L of between about 0.16 and about 0.19 millimeters. Further, as discussed above, it is desirable that the fitting 56 be spaced a distance D away from the inner surface 53 of the closure plate substrate 52 so that a spaced-relationship is maintained between the upper surface 51 of the fitting 56 and the inner surface 53 of the substrate 52 when the closure plate 50 has been properly secured to the outer face 105 as depicted in FIG. 2B. According to some implementations the distance D (see FIG. 6) is between about 0.1 to about 10.0 millimeters, and preferably between about 0.2 to about 1.5 millimeters. In some implementations the closure plate substrate 52 comprises an elliptical shape having both major and minor dimensions that fall within the about 16 to about 23 millimeter range.

Figure 9:
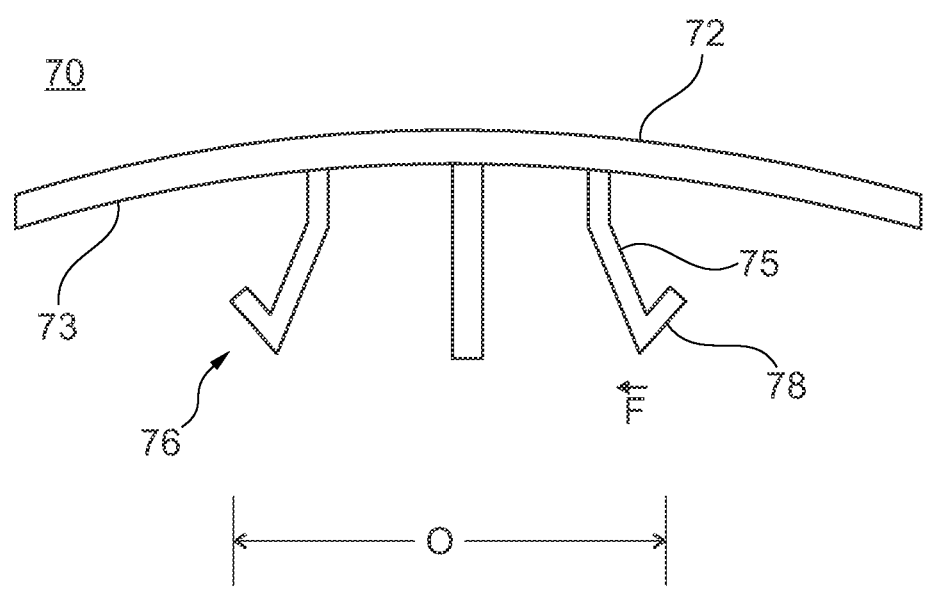
FIG. 9 illustrates a closure plate according to an implementation.

FIG. 9 illustrates a closure plate 70 according to other implementations wherein the burr hole fitting 76 comprises three or more arm segments 75 extending downward from the inner surface 73 of the closure plate substrate 72. One or more of the arm segments 75 are capable of being flexed inward as denoted by the arrow F. The ends 78 of the arms are adapted for engaging the inner wall 101 of the burr hole 100 when the closure plate has been properly positioned and fitted on the outer surface 105 of the scalp of the patient. The outer dimension O of the fitting 76 is slightly greater than the outer dimension of the burr hole prior to the fitting being inserted therein. In use with a bore hole produced by a 14 millimeter drill, the outer dimension O of fitting 76 is between about 14.45 and about 14.40 millimeters in some implementations. In some implementations the arms 75 are formed integrally and as a single piece with the closure pate substrate 72 (such as by injection molding), while in other implementations the arms 75 are formed separately from the substrate 72 and are attached thereto. In the latter case, the arms 75 may comprise a set of metallic arms that are interconnected by a metallic ring at their ends opposite the ends 78. In such an implementation, the ring that connects the arms 75 may be attached to the bottom side 73 of the closure plate substrate 72. According to one implementation the arm assembly 75 is comprises of a metal material and the closure plate substrate 72 comprises a plastic material, such as PEEK.

FIGS. 10-13 depict a bone flap fixation assembly 200 according to other implementations. The assembly includes a support plate 82 and a closure plate 90 that are connected by first and second flexible strip segments 86a and 86b. As will be discussed in more detail below, the closure plate 90 is moveable along the flexible strip segments in a direction toward the support plate 82 as indicated by the arrow in FIG. 10. The flexible strip segments 86a, 86b are coupled to the support plate 82 and extend upward so that their ends are coupled with or otherwise fitted into respective end sections 202, 203 of a handle 201. The assembly 200 is further equipped with a force applicator 110 that rides on the first and second flexible strip segments 86a, 86b between the handle 201 and the closure plate 90. The force applicator 110 is adapted with regions 112 for receiving the thumb and index finger of a user. In use, when the assembly is in a ready position, as shown in FIG. 10, with the bone flap properly situated between the support plate 82 and the closure plate 90, the user applies with the thumb and index finger a downward force to regions 112, while holding the handle 201 with the other hand, to cause the bottom surfaces 114 of the applicator 110 is be urged against a topside surface of the closure plate 90. Sufficient force is applied to cause the closure plate 90 to be moved against a resistance that exist between it and the flexible strip segments 86a, 86b and towards the support plate 82. At a point in time when the bone flap has been properly secured in place by the support and closure plates, the flexible strips 86a, 86b are cut at a location above the topside surface of the closure plate 90 and the handle 201 and force applicator 110 are removed. Lastly, the flexible strip segments 86a, 86b are severed at the topside surface of the closure plate 90 so that little or no portion of the flexible strip segments extends upward from the closure plate. As shown in FIG. 10, the closure plate 90 comprises a substrate 92, a spacer 94 and a burr hole fitting 96. The burr hole fitting 96 is spaced a distance below the substrate 92, the spacing in the present instance being provided by a spacer 94. The purpose and function of the fitting 96 is consistent with those previously disclosed herein.

Figure 11A:
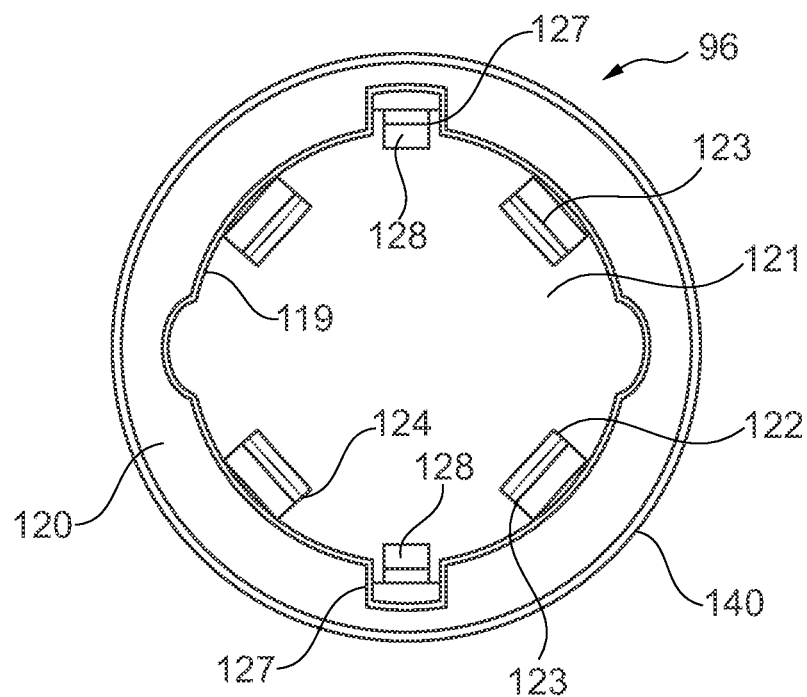
FIGS. 11A and 11B are bottom and perspective views, respectively, of the burr hole fitting depicted in FIG. 10.
Figure 11B:
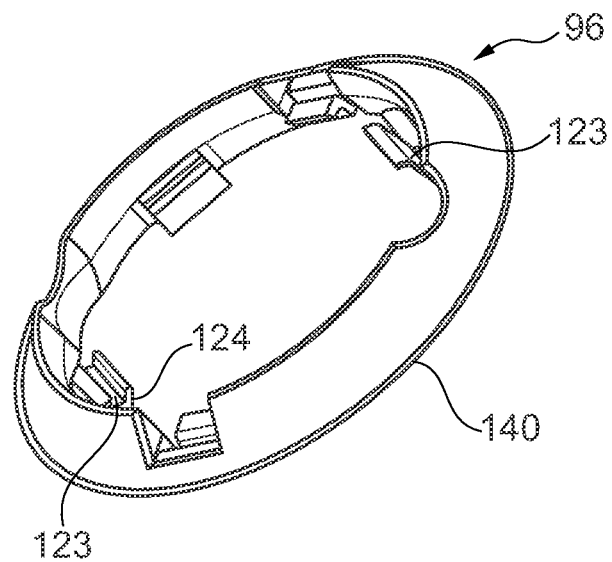

FIGS. 11A and 11B show bottom and perspective views, respectively, of the burr hole fitting 96 according to one implementation. The fitting comprises a circular ring-like structure 120 made from a thin polymeric material, such as PEEK. The ring 120 has sufficient hoop strength to generally maintain its circular configuration during use. In some implementations at least certain regions of the ring structure 120 are adapted to flex inward toward the center of the ring when a force is peripherally applied to the ring. Formed integrally and as a single piece with the ring 120 are one or more support tabs 122 and one or more fastening tabs 126. In the implementation shown, the ring 120 is equipped with four support tabs 122 and two fastening tabs 126. Each of the support tabs 122 comprises a component 124 that extends downward and inward in a direction towards the center of the ring opening 121. According to some implementations the support tabs 122 are constructed so that the components 124 are able to be flexed inward toward the inner circumference 119 of the ring 120 as will be discussed in more detail below. In some implementations the support tabs 122 also are used to establish the horizontal position of the ring 120 on the closure plate 90 so as to assist in maintaining a spaced-apart relationship between the upper surface of the ring 121 and the inner surface 130 of the substrate 92 as discussed above. In some implementations a groove or gap 123 is provided in a bottom face of the support tab 122 between the component 124 and the outer circumference 119 of the ring 120. The fastening tabs 126 extend in a horizontal direction into the ring opening 121. Each of the fastening tabs 126 includes an inwardly protruding elastic component 127 that has disposed at an end thereof a latching member 128 adapted for engaging with a cooperating part of the closure plate 90 to secure the ring 120 structure thereto.

Figure 12A:
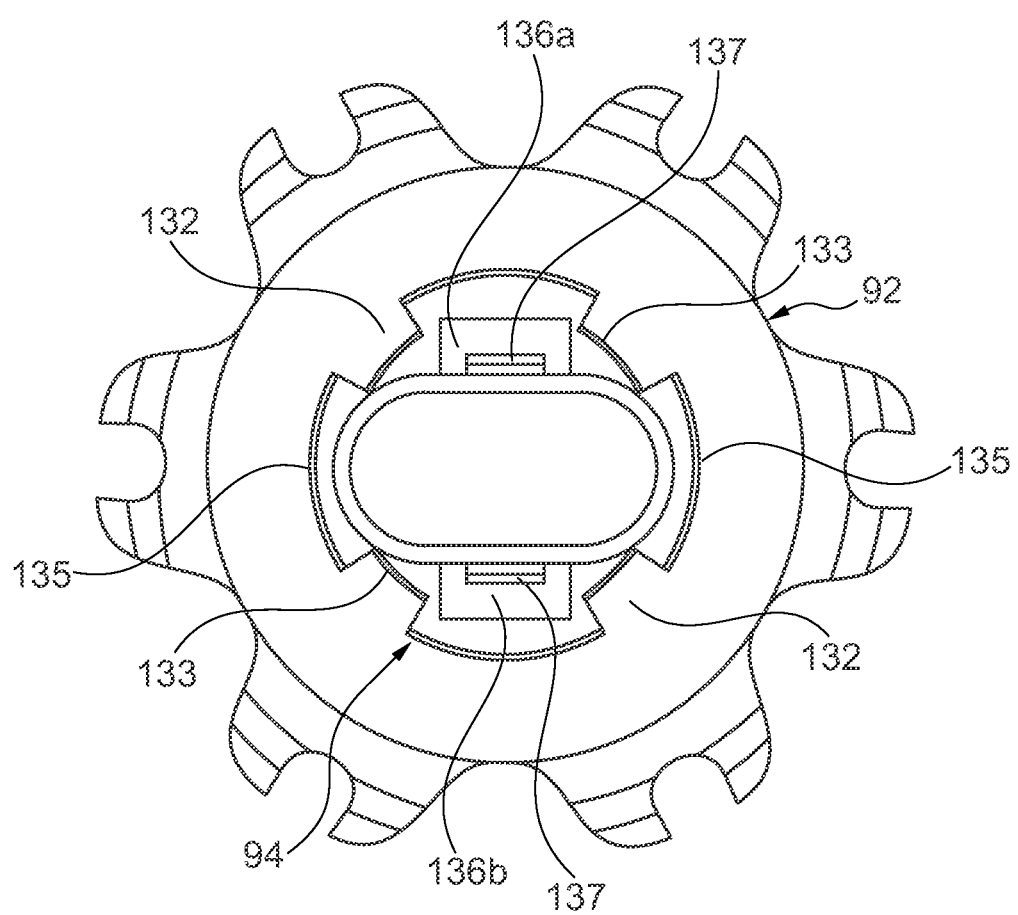
FIG. 12A illustrates a bottom view of the closure plate substrate depicted in FIG. 10.
Figure 12B:
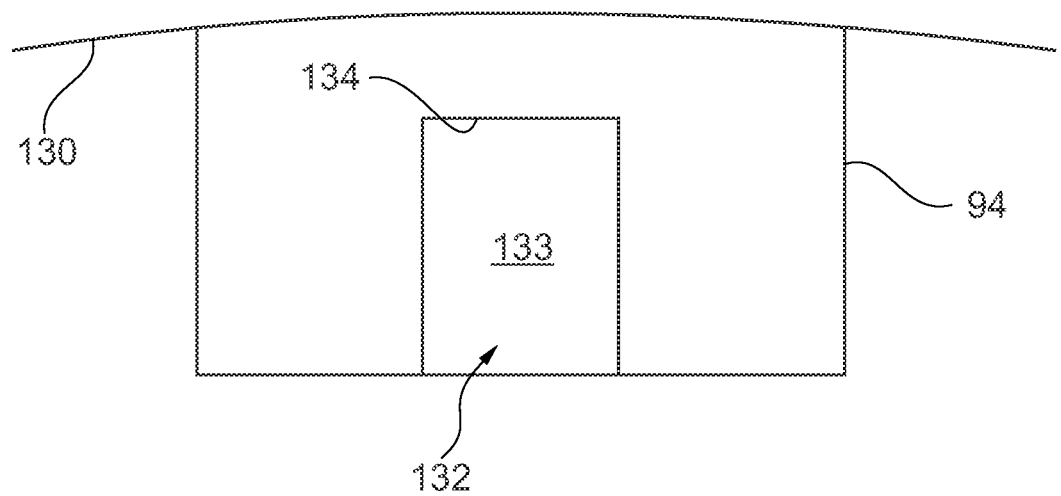
FIG. 12B illustrates a side view of a section of a spacer according to an implementation.

The burr hole fitting 96 is connected to the closure plate substrate 92 via a spacer 94 in the form of a column-like structure having a length that extends downward from the inner surface 130 of the closure plate substrate 92. As shown in FIGS. 12A and 12B, the spacer 94 includes receptacles 132 for receiving the support tabs 122. In some implementations the dimensional characteristics of the support tabs 122 and the receptacles 132 prevent the fitting 96 from being rotated with respect to the closure plate substrate 92, while in other implementations the dimensional characteristics allow for a degree of rotation in the range of, for example, 0 to 10 degrees. As discussed above, in some implementations a function of the support tabs 122 is to establish the horizontal position of the ring 120 on the closure plate 90 so as to maintain a spaced-apart relationship between the upper surface of the ring 121 and the inner surface 130 of the substrate 92. In accordance with achieving this function, in some implementations the receptacles 132 comprise an upper wall 134 adapted for interfacing with an upper face of the support tab 122, the upper wall 134 situated a distance away from the inner surface 130 of the closure plate substrate 92 as shown in FIG. 12B. Thus, in accordance with such an implementation the horizontal position of the fitting 96 is established by the upper face of the support tab 122 interfacing with the upper wall 134 of the receptacle 132. Provided within each of the column walls 135 of the spacer 94 is a part (not shown) configured to cooperate with the latching member 128 of the fastening tab 126 to lock the fitting 96 onto the closure plate 90.

As noted above, in some implementations the support tabs 122 comprise a sloped component 124, In such implementations the facing wall 133 of the receptacles 132 in the spacer 94 are similarly sloped to receive the sloped component 124. In some implementations the slope of component 124 is greater than the slope of the facing wall 133. In such implementations, the groove or gap 123 of the support tab 122 provides the component 124 with a degree of flexibility to permit the inner face of the component 124 to at least partially or fully adapt to the slope of the facing wall 133.

Figure 13A:
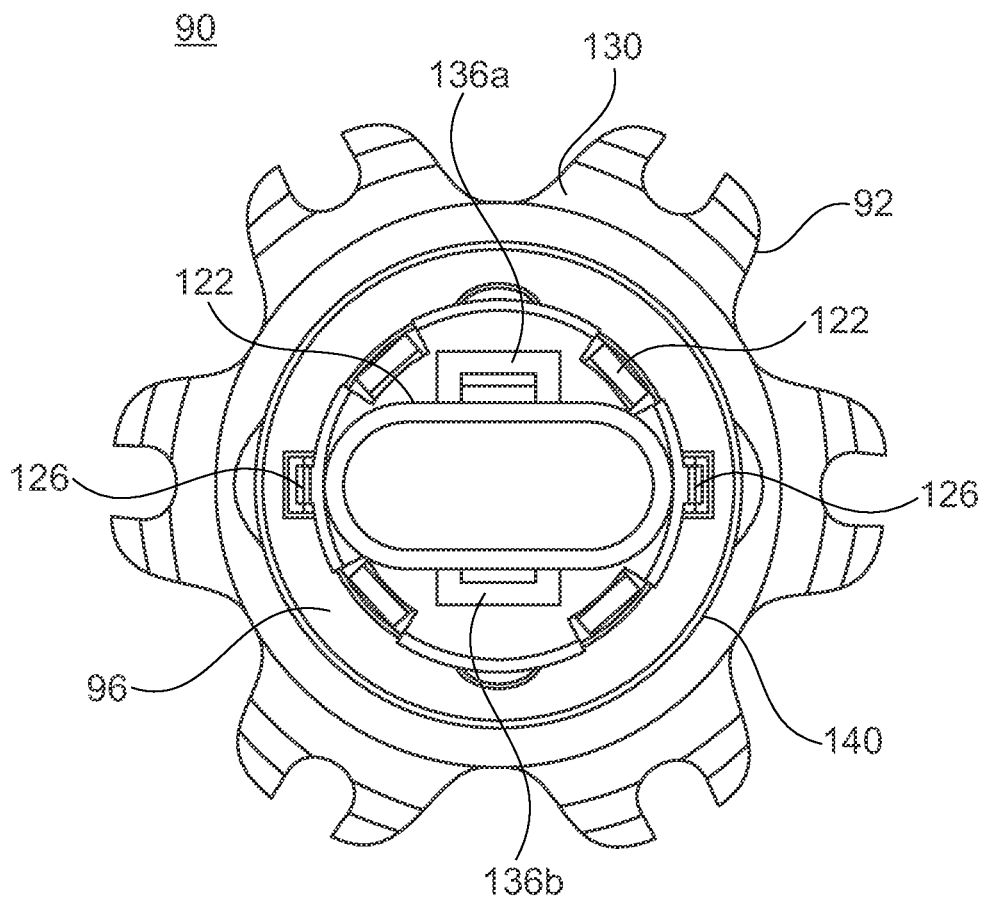
FIGS. 13A and 13B are bottom and perspective views, respectively, of the burr hole fitting of FIG. 12 attached to the closure plate substrate of FIG. 11.
Figure 13B:
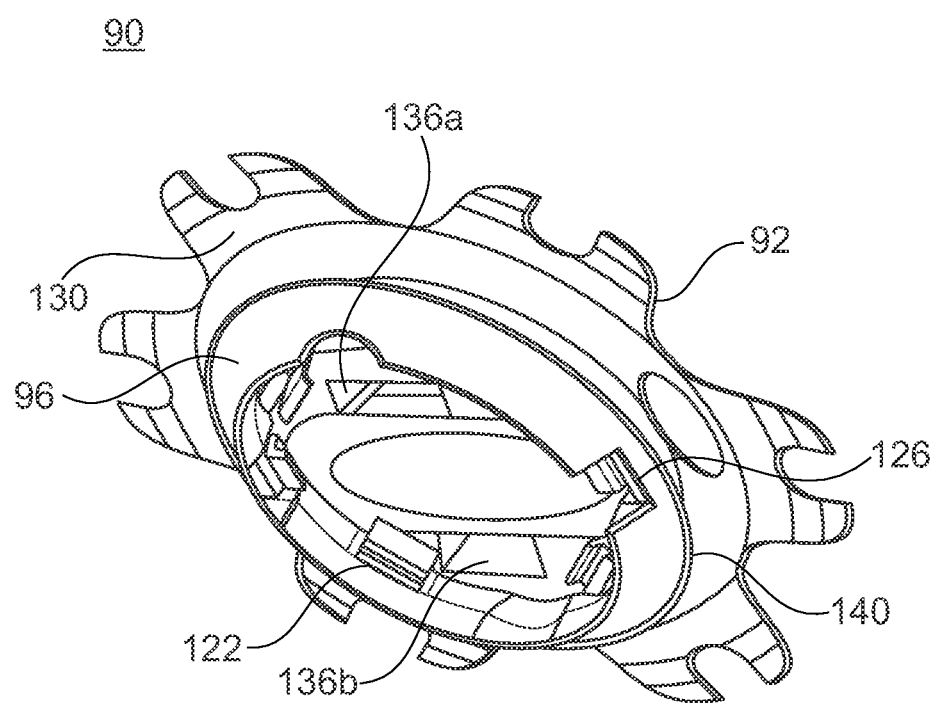

FIGS. 13A and 13B show a bottom view and a perspective view, respectively, of the fitting closure plate 90 with the fitting 96 arranged thereon.

Turning again to FIG. 12A, the closure plate 90 has two openings 136a, 136b extending there through that are adapted to respectively receive flexible strip segments 86a, 86b. According to one implementation, each of the flexible strip segments 86a, 86b comprises ratchet teeth on a face thereof adapted for engaging with an interlocking feature 137 associated with each of openings 136a and 136b. The manner in which the ratchet teeth of the flexible strip segments 86a, 86b engage with the respective interlocking features 137 permits the passage and movement of flexible strip segments 86a, 86b in a first direction through the respective openings 136a, 136b while preventing movement of the flexible strip segments 86a, 86b in a second direction opposite the first direction. In other words, in some implementations the closure plate 90 is moveable only in the direction of the arrow shown in FIG. 10.

As with some of the implementations disclosed above, the fitting 96 may be equipped with a peripheral lip 140 that has a diameter/outer dimension that is equal to, or preferably slightly greater than that of the burr hole 100 to which the fitting is intended to be inserted. The peripheral lip 140 is adapted to flex and/or be compress in order to be pressed or to otherwise rest against the inner wall 101 of the burr hole 100 when the fitting 140 is inserted therein. In some implementations the peripheral lip 140 is integrally formed as a single piece with the ring structure 120. In other implementations the lip 140 is formed separately from the support structure 120 and is attached or otherwise coupled thereto as discussed above.

Figure 4A:
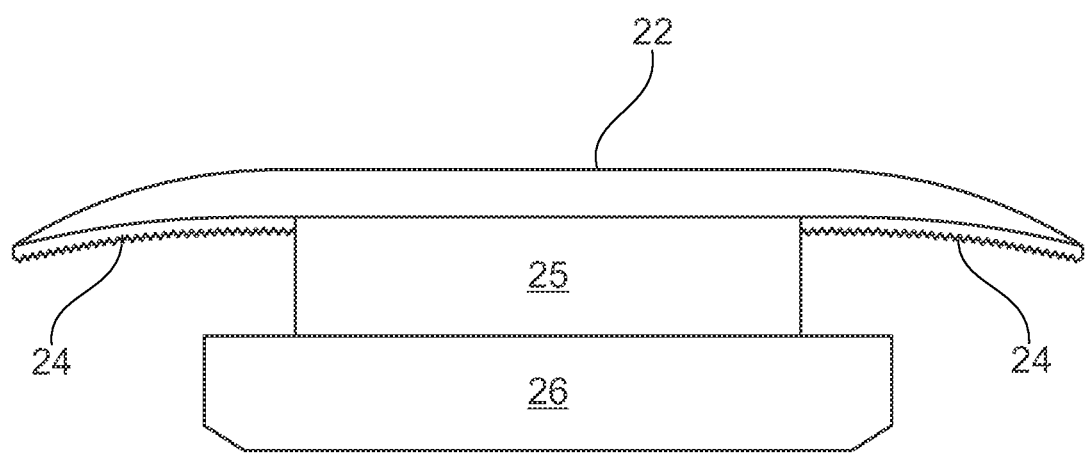
FIGS. 4A and 4B illustrate closure plates according to some implementations wherein the inner surface of the closure plate is provided with means for inhibiting slip of the closure plate on the scalp of the patient upon the closure plate being attached thereto.
Figure 4B:
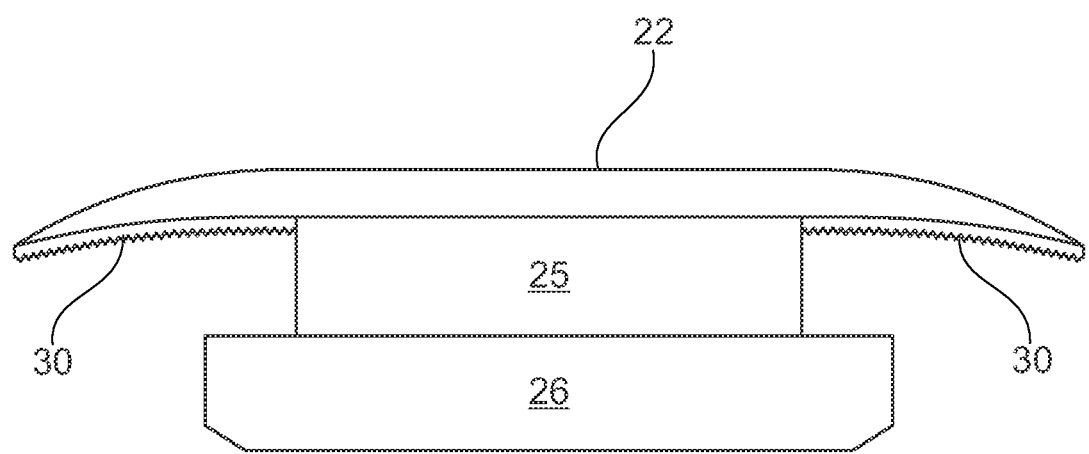

Further, as with the implementations of FIGS. 4A and 4B, in instances when the closure plate substrate 22 is made of a polymeric material, such as PEEK, the inner surface 130 of the closure plate substrate 92 may be treated or otherwise provided with a slip-resistant a lining, coating, or the like.

According to some implementations the closure plate substrate 90 has a diameter of between about 16 to about 23 millimeters. In an implementation where a peripheral lip 140 is provided on the fitting 96, the diameter of the burr hole fitting 96 as measured from the outer bounds of the peripheral lip 140 in such applications may be in some implementations between about 14.35 to about 14.40 millimeters. According to some implementations the peripheral lip 140 has a thickness T of about 0.05 millimeters and a length L of between about 0.16 and about 0.19 millimeters. Further, as discussed above, it is desirable that the fitting 56 be spaced a distance away from the inner surface 130 of the closure plate substrate 92 so that a spaced-relationship is maintained between the upper surface 121 of the fitting 96 and the inner surface 130 of the substrate 22 when the closure plate 90 has been properly secured to the outer face 105. According to some implementations the distance is between about 0.1 to about 10.0 millimeters, and preferably between about 0.2 to about 1.5 millimeters.

Figure 14:
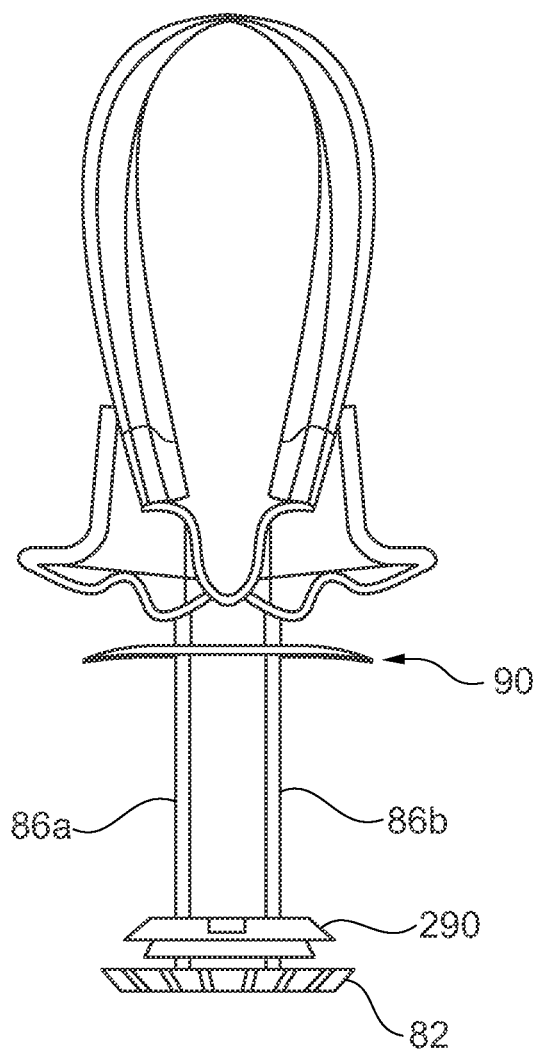
FIG. 14 illustrates a fixation device according to other implementations wherein a burr hole fitting is coupled with the support plate.
Figure 15:
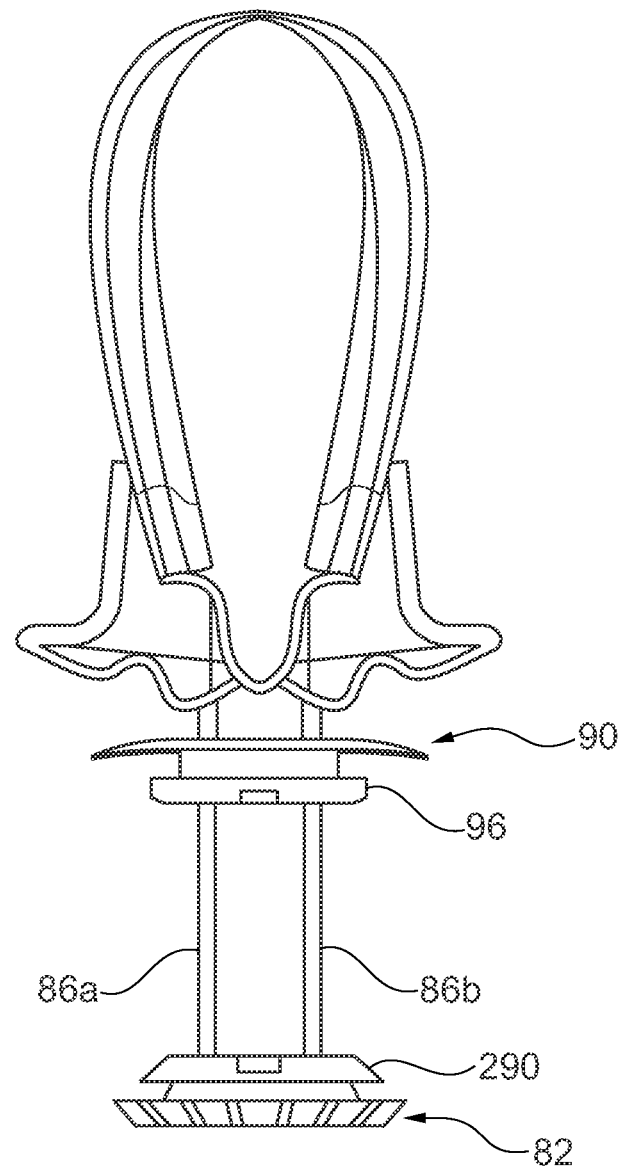
FIG. 15 illustrates a fixation device according to other implementations wherein each of the closure plate and support plate have an associated burr hole fitting.
Figure 16:
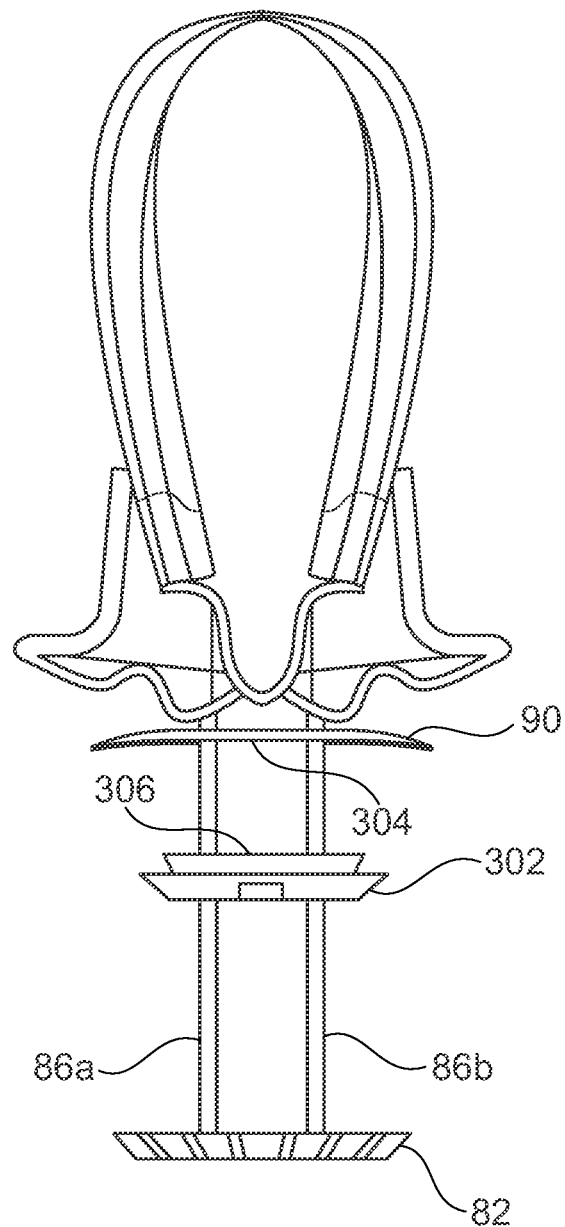
FIG. 16 illustrates a fixation device according to other implementations.

In the preceding text a multitude of burr hole fitting implementations have been described with the burr hole fitting being association with the part of the fixation device referred to herein as the "closure plate". It is appreciated, however, that the present invention is not limited to the burr hole fitting being attached to or otherwise coupled with the closure plate. For example, as shown in FIG. 14, a burr hole fitting 290 may alternatively be attached to or otherwise coupled with the support plate 82. The attachment or coupling of the burr hole fitting 290 to the support plate 82 may be accomplished in a manner similar to the numerous implementations disclosed above with respect to the burr hole fitting being attached to or coupled with the closure plate. In such implementations, the burr hole fitting 290 may be fixed in a position above the support plate 82 with no ability to be moved along the length of the strip segments 86a and 86b. In other implementations the burr hole fittings 96 and 290 may be respectively provided on the closure plate 90 and the support plate 82 as shown in FIG. 15. In yet other implementations, a fixation device is provided, as shown in FIG. 16, where the burr hole fitting 302 resides on the flexible strips 86a and 86b in a position between the closure plate 90 and support plate 82 when the fixation device is in a ready to use configuration. In such implementations the burr hole fitting 302 is slideable on the flexible strips 86a and 86b in a direction towards the support plate 82. Hence, in use, as the closure plate 90 is advanced downward towards the support plate 82, a bottom portion 304 of the closure plate 90 comes into contact with an upper portion 306 of the burr hole fitting 302 to cause the burr hole fitting 302 to be moved along with it towards the support plate 82. In such implementations a spacer 304 located on one or both of the closure plate 90 and the burr hole fitting 302 causes there to be a spaced-apart relationship between the closure plate substrate 92 and the fitting 302 when the closure plate substrate is firmly pressed against the outer surface 105 of the patient's scalp.

While the above description contains many specifics, those specifics should not be construed as limitations on the scope of the disclosure, but merely as exemplifications of preferred implementations thereof. Moreover, for the sake of clarity, not every conceivable combination of a closure plate substrate, spacer and fitting has been disclosed. However, it is appreciated that many of the features disclosed herein are interchangeable among the various implementations. Those skilled in the art will envision many other possible variations that are within the scope and spirit of the disclosure. Further, it is to be appreciated that the manner in which the closure plate and support plate are connected and moveable with respect to one another is not limited to those disclosed herein.

What is claimed is:

1. A closure plate for use in fixating a cranial bone flap with a cranial bone mass at the location of a burr hole having an inner wall, the closure plate comprising:
    a substrate having an outer surface and an inner surface, at least a portion of the inner surface adapted to be applied against an outer face of outer edges of the cranial bone mass and the cranial bone flap at the location of the burr hole; and
    a burr hole fitting coupled to and spaced a distance below the inner surface of the substrate and adapted for being inserted entirely into the burr hole, the burr hole fitting being coupled with the substrate via a spacer, the burr hole fitting comprising one or more peripheral portions adapted for being pressed or rested against the inner wall of the burr hole when the fitting is inserted therein, the one or more peripheral portions endowed with a freedom of movement, the freedom of movement of the one or more peripheral portions enabling the fitting to be inserted into the burr hole, wherein the burr hole fitting comprises a body having an internal cavity defined by one or more inner surfaces of the body, the body further comprising one or more support tabs that each extend from the one or more inner surfaces of the body, the spacer having one or more first receptacles for respectively receiving the one or more support tabs, the one or more receptacles and the one or more support tabs having cooperative features that cause the burr hole fitting to be spaced the distance below the inner surface of the substrate when the burr hole fitting is assembled onto the spacer.

2. A closure plate according to claim 1, wherein the body has a peripheral flexible lip that extends radially from at least a portion of the body, the flexible lip constituting, at least in part, the one or more peripheral portions.

3. A closure plate according to claim 2, wherein the body comprises a substantially circular ring that is centrally aligned with the substrate.

4. A closure plate according to claim 2, wherein the body is substantially rigid.

5. A closure plate according to claim 1, wherein the body has one or more circumferentially spaced-apart peripheral flexible lips extending radially from the body, the one or more flexible lips constituting, at least in part, the one or more peripheral portions.

6. A closure plate according to claim 1, wherein the body has one or more sections that are capable of being moved radially inward, the one or more peripheral portions being an outer surface of the one or more sections of the body.

7. A closure plate according to claim 1, wherein the body has one or more sections that are capable of being flexed radially inward.

8. A closure plate according to claim 1, where in the body has a resilient outer surface, the resilient surface constituting the one or more peripheral portions.

9. A closure plate according to claim 1, wherein at least a portion of the inner surface of the substrate is lined or coated with a slip resistant material.

10. A closure plate according to claim 1, wherein the one or more peripheral portions endowed with a freedom of movement comprises a peripheral lip situated on an external peripheral region of the body, the peripheral lip adapted to flex inward when the burr hole fitting is inserted into the burr hole.

11. A closure plate according to claim 1, wherein the spacer has one or more features that respectively cooperate with the one or more support tabs to lock the burr hole fitting onto the spacer when the burr hole fitting is assembled onto the spacer, the one or more peripheral portions endowed with a freedom of movement comprising a peripheral lip situated on an external peripheral region of the body, the peripheral lip adapted to flex and/or be compressed inward when the burr hole fitting is inserted into the burr hole.

12. A closure plate according to claim 1, wherein the spacer has one or more features that respectively cooperate with the one or more support tabs to lock the burr hole fitting onto the spacer when the burr hole fitting is assembled onto the spacer, the one or more peripheral portions endowed with a freedom of movement comprising a peripheral lip situated on an external peripheral region of the body, the peripheral lip adapted to be compressed radially inward when the burr hole fitting is inserted into the burr hole.

13. A fixation device for fixating a cranial bone flap with a cranial bone mass at the location of a burr hole having an inner wall, the fixation device comprising:
a support plate having an inner surface that is adapted to be applied against an inner face of outer edges of the cranial bone mass and the cranial bone flap at the location of the burr hole, the inner surface having an overall peripheral profile defined at least in part by first and second peripheral edges, the overall peripheral profile being of a size sufficient for at least portions of the inner surface to extend across the outer edges of the cranial bone mass and the cranial bone flap at the location of the burr hole;
a first flexible strip segment extending from the first peripheral edge of the support plate and a second flexible strip segment extending from the second peripheral edge of the support plate; and
a closure plate comprising a substrate having an outer surface and an inner surface, the inner surface adapted to be applied against the an outer face of the outer edges of the cranial bone mass and the cranial bone flap at the location of the burr hole, the closure plate having first and second openings extending there through, each of the first and second openings respectively receiving the first and second flexible strip segments, each of the first and second openings having associated therewith an interlocking feature that permits the passage and movement of the first and second flexible strip segments in a first direction through the respective first and second openings while preventing movement of the first and second flexible strip segments in a second direction opposite the first direction, the closure plate being moveable along the first and second flexible strips in a direction toward the support plate, the closure plate further comprising a burr hole fitting coupled with and spaced a distance below the inner surface of the substrate and adapted for being inserted entirely into the burr hole, the fitting comprising one or more peripheral portions adapted for being pressed against or rest on the inner wall of the burr hole when the fitting is inserted therein, the one or more peripheral portions endowed with a freedom of movement, the freedom of movement of the one or more peripheral portions enabling the fitting to be inserted into the burr hole.

14. A fixation device according to claim 13, wherein the burr hole fitting comprises a body having a peripheral flexible lip that extends radially from at least a portion of the body, the flexible lip constituting, at least in part, the one or more peripheral portions.

15. A fixation device according to claim 14, wherein the body comprises a substantially circular ring that is centrally aligned with the substrate.

16. A fixation device according to claim 14, wherein the body is substantially rigid.

17. A fixation device according to claim 13, wherein the burr hole fitting comprises a body having one or more circumferentially spaced-apart peripheral flexible lips extending radially from the body, the one or more flexible lips constituting, at least in part, the one or more peripheral portions.

18. A fixation device according to claim 13, wherein the burr hole fitting comprises a body having one or more sections that are capable of being moved radially inward, the one or more peripheral portions being an outer surface of the one or more sections of the body.

19. A fixation device according to claim 13, wherein the burr hole fitting comprises a body having one or more sections that are capable of being flexed radially inward.

20. A fixation device according to claim 13, wherein the fitting comprises a body having a resilient outer surface, the resilient surface constituting the one or more peripheral portions.

21. A fixation device according to claim 13, wherein at least a portion of the inner surface of the substrate is lined or coated with a slip resistant material.

22. A fixation device according to claim 13, wherein the burr hole fitting is coupled with the substrate via a spacer.

23. A fixation device according to claim 22, wherein the burr hole fitting comprises a body having an internal cavity defined by one or more inner surfaces of the body, the body further comprising one or more support tabs that each extend from the one or more inner surfaces of the body, the spacer having one or more first receptacles for respectively receiving the one or more support tabs, the one or more receptacles and the one or more support tabs having cooperative features that cause the burr hole fitting to be spaced the distance below the inner surface of the substrate when the burr hole fitting is assembled onto the spacer.

24. A fixation device according to claim 23, wherein the body further comprises one or more fastening tabs that each extend from the one or more inner surfaces of the body, the spacer having one or more features that respectively cooperate with the one or more fastening tabs to lock the burr hole fitting onto the spacer when the burr hole fitting is assembled onto the spacer.

25. A fixation device according to claim 23, wherein the one or more peripheral portions endowed with a freedom of movement comprises a peripheral lip situated on an external peripheral region of the body, the peripheral lip adapted to flex inward when the burr hole fitting is inserted into the burr hole.

26. A fixation device according to claim 22, wherein the burr hole fitting comprises a body having an internal cavity defined by one or more inner surfaces of the body, the body further comprising one or more support tabs and one or more fastening tabs that each extend from the one or more inner surfaces of the body, the spacer having one or more first receptacles for respectively receiving the one or more support tabs, the one or more receptacles and the one or more support tabs having cooperative features that cause the burr hole fitting to be spaced the distance below the inner surface of the substrate when the burr hole fitting is assembled onto the spacer, the spacer having one or more features that respectively cooperate with the one or more fastening tabs to lock the burr hole fitting onto the spacer when the burr hole fitting is assembled onto the spacer, the one or more peripheral portions endowed with a freedom of movement comprising a peripheral lip situated on an external peripheral region of the body, the peripheral lip adapted to flex when the burr hole fitting is inserted into the burr hole.

27. A fixation device according to claim 22, wherein the burr hole fitting comprises a body having an internal cavity defined by one or more inner surfaces of the body, the body further comprising one or more support tabs and one or more fastening tabs that each extend from the one or more inner surfaces of the body, the spacer having one or more first receptacles for respectively receiving the one or more support tabs, the one or more receptacles and the one or more support tabs having cooperative features that cause the burr hole fitting to be spaced the distance below the inner surface of the substrate when the burr hole fitting is assembled onto the spacer, the spacer having one or more features that respectively cooperate with the one or more fastening tabs to lock the burr hole fitting onto the spacer when the burr hole fitting is assembled onto the spacer, the one or more peripheral portions endowed with a freedom of movement comprising a peripheral lip situated on an external peripheral region of the body, the peripheral lip adapted to be compressed radially inward when the burr hole fitting is inserted into the burr hole.

28. A support plate for use in fixating a cranial bone flap with a cranial bone mass at the location of a burr hole having an inner wall, the support plate comprising:
  a substrate having an outer surface and an inner surface, at least a portion of the inner surface adapted to be applied against an inner face of outer edges of the cranial bone mass and the cranial bone flap at the location of the burr hole; and
  a burr hole fitting coupled to and spaced a distance above the inner surface of the substrate and adapted for residing entirely within the burr hole, the burr hole fitting being coupled with the substrate via a spacer, the burr hole fitting comprising one or more peripheral portions adapted for being pressed or rested against the inner wall of the burr hole when the fitting resides therein, the one or more peripheral portions endowed with a freedom of movement, the freedom of movement of the one or more peripheral portions enabling the fitting to reside within the burr hole, wherein the burr hole fitting comprises a body having an internal cavity defined by one or more inner surfaces of the body, the body further comprising one or more support tabs that each extend from the one or more inner surfaces of the body, the spacer having one or more first receptacles for respectively receiving the one or more support tabs, the one or more receptacles and the one or more support tabs having cooperative features that cause the burr hole fitting to be spaced the distance above the inner surface of the substrate when the burr hole fitting is assembled onto the spacer.

29. A support plate according to claim 28, wherein the body has a peripheral flexible lip that extends radially from at least a portion of the body, the flexible lip constituting, at least in part, the one or more peripheral portions.

30. A support plate according to claim 29, wherein the body comprises a substantially circular ring that is centrally aligned with the substrate.

31. A support plate according to claim 29, wherein the body is substantially rigid.

32. A support plate according to claim 28, wherein the body has one or more circumferentially spaced-apart peripheral flexible lips extending radially from the body, the one or more flexible lips constituting, at least in part, the one or more peripheral portions.

33. A support plate according to claim 28, wherein the body has one or more sections that are capable of being moved radially inward, the one or more peripheral portions being an outer surface of the one or more sections of the body.

34. A support plate according to claim 28, wherein the body has one or more sections that are capable of being flexed radially inward.

35. A support plate according to claim 28, wherein the body has a resilient outer surface, the resilient surface constituting the one or more peripheral portions.

36. A support plate according to claim 28, wherein at least a portion of the inner surface of the substrate is lined or coated with a slip resistant material.

37. A support plate according to claim 28, wherein the one or more peripheral portions endowed with a freedom of movement comprises a peripheral lip situated on an external peripheral region of the body, the peripheral lip adapted to flex inward when the burr hole fitting is inserted into the burr hole.

* * * * *